United States Patent [19]

Fex et al.

[11] Patent Number: 4,937,245

[45] Date of Patent: Jun. 26, 1990

[54] BISPHENYLALKYLPIPERAZINE DERIVATIVES, A METHOD OF THEIR PREPARATION AND A PHARMACEUTICAL PREPARATION

[76] Inventors: Tomas Fex, Spårsnögatan 26, S-222 52 Lund; Knut G. Olsson, Baltzarsgatan 2, S-211 36 Malmö; Aina L. Abramo, Järavallsvägen 30 A, S-237 00 Bjärred; Erik G. Christensson, Nils Bjelkegatan 3 A, S-222 20 Lund; Torbjörn E. Lundstedt, Gökblomstervägen 37, S-24041 Löddeköpinge, all of Sweden

[21] Appl. No.: 282,130

[22] PCT Filed: Mar. 25, 1988

[86] PCT No.: PCT/SE88/00144

§ 371 Date: Nov. 30, 1988

§ 102(e) Date: Nov. 30, 1988

[87] PCT Pub. No.: WO88/07528

PCT Pub. Date: Oct. 6, 1988

[30] Foreign Application Priority Data

Apr. 2, 1987 [SE] Sweden .................................. 8701375

[51] Int. Cl.$^5$ ................. A61K 31/495; A61K 31/505; C07D 401/06; C07D 403/06
[52] U.S. Cl. ..................................... 514/252; 514/218; 514/235.8; 540/481; 540/575; 540/598; 544/121; 544/295; 544/360; 544/364
[58] Field of Search ............... 544/121, 295, 360, 364; 540/575, 481, 598; 514/218, 235.8, 252

[56] References Cited

U.S. PATENT DOCUMENTS

| | | | |
|---|---|---|---|
| 2,958,694 | 11/1960 | Janssen | 544/360 |
| 2,979,508 | 4/1961 | Janssen | 544/360 |
| 2,985,657 | 5/1961 | Janssen | 544/360 |
| 4,766,215 | 8/1988 | Abou-Gharbia et al. | 544/295 |

FOREIGN PATENT DOCUMENTS

| | | | |
|---|---|---|---|
| 3507983 | 9/1985 | Fed. Rep. of Germany | |
| 81167 | 5/1985 | Japan | 544/295 |
| 3146872 | 6/1988 | Japan | 544/295 |
| 7528 | 10/1988 | World Int. Prop. O. | 544/295 |

OTHER PUBLICATIONS

Fex et al, CA 110-95280t (1989).
Leysen, J. E., et al., "[$^3$H]ketanserin, A Selective $^3$H-Ligand for Serotonin$_2$ Receptor Binding Sites: Binding Properties, Brain Distribution, and Functional Role," *Mol. Pharmacol.* 21: 301-314, 1982.

*Primary Examiner*—Cecilia Shen
*Attorney, Agent, or Firm*—Scully, Scott, Murphy & Presser

[57] ABSTRACT

A compound having the formula (I) or a pharmaceutically acceptable salt thereof:

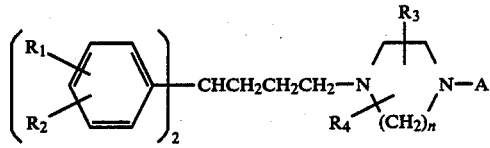

wherein all the symbols are defined in the specification; having valuable pharmaceutical properties, useful for the treatment of mental disorders, such as psychoses, depression and anxiety.

16 Claims, No Drawings

BISPHENYLALKYLPIPERAZINE DERIVATIVES, A METHOD OF THEIR PREPARATION AND A PHARMACEUTICAL PREPARATION

BACKGROUND

There is an urgent need for novel drugs in the treatment of mental disorders which are more effective and which have fewer side effects than the drugs in clinical use today. Antipsychotic drugs in current use produce a range of troublesome extrapyramidal movement disorders (e.g. acute dystonic reactions and tardive dyskinesia) and are poor in ameliorating the negative symptoms (e.g. restricted or blunted emotional arousal) of schizophrenia. The main disadvantage of the antidepressants is that they fail to alleviate depression in 30 to 40% of patients. Anxiolytics are commonly associated with addictive properties.

PRIOR ART

Various pyridyl- and pyrimidyl-piperazine derivatives pharmacologically active in the central nervous system are known in the art. Some representative examples can be mentioned. Azaperone, a neuroleptic drug of the butyrophenone series, is a sedative for pigs. Buspirone is an anxiolytic. The anxiolytic effect is thought to be mediated via effects on the 5HT-receptors.

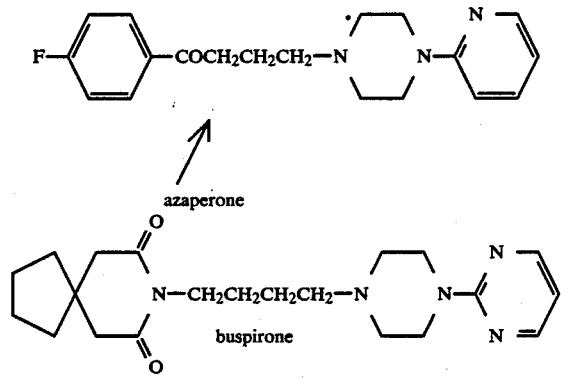

DESCRIPITON OF THE INVENTION

Pyridyl- and pyrimidyl-piperazines substituted in the 4-position of the piperazine ring with a highly lipophilic diphenyl-butyl group have unexpectedly been found to exhibit pharmacological properties superior to compounds known in the art.

According to the invention there are provided novel compounds having the general formula (I).

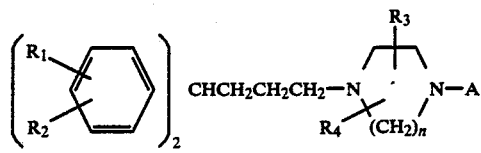

wherein $R_1$ and $R_2$ are the same or different and selcted from hydrogen and halogen;
$R_3$ and $R_4$ are the same or different and selected from hydrogen and lower alkyl;
n is 2 or 3;

A is selected from the following pyrimidyl or pyridyl groups

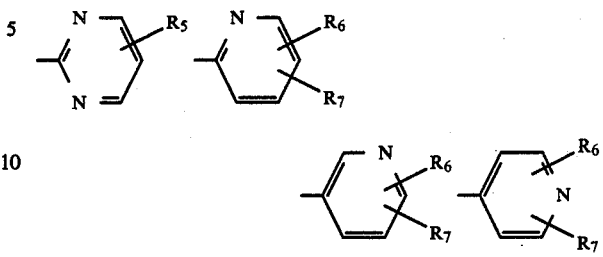

wherein $R_5$ is selected from hydrogen, lower alkyl or halogen; $R_6$ and $R_7$ are the same or different and selected from hydrogen, halogen, lower alkyl, electron donor groups such as lower alkoxy or hydroxy, electron acceptor groups such as cyano, nitro, trifluoromethyl, $COOR_8$, $CONR_9R_{10}$ or CO—B; wherein $R_8$ is hydrogen or lower alkyl; $R_9$ and $R_{10}$ are the same or different and selected from hydrogen, lower alkyl and cycloalkyl;
B is selected from

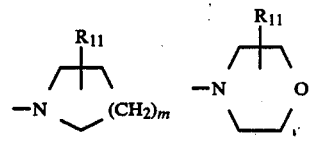

wherein m is 1, 2, 3 or 4.
$R_{11}$ is selected from hydrogen or lower alkyl, and the pharmacologically active salts thereof,
and when used in the foregoing definitions the term lower alkyl is meant to include straight and branched, saturated and unsaturated hydrocarbon groups having from 1 to 5 carbon atoms;
the term cycloalkyl is meant to include cyclic, saturated and unsaturated hydrocarbon groups having from 3 to 8 carbon atoms;
the term lower alkoxy is meant to include straight or branched, saturated or unsaturated alkoxy groups having from 1 to 5 carbon atoms;
the term halogen is meant to include fluoro, chloro and bromo.

It is preferred that one of $R_1$ and $R_2$ is different from hydrogen and when one or both of $R_1$ and $R_2$ are halogen fluoro is preferred.

As regards $R_3$ and $R_4$ hydrogen or methyl are preferred, especially hydrogen.

As regards $R_5$ hydrogen, methyl, or halogen, especially fluoro, is preferred.

As regards $R_6$ hydrogen, methyl, alkoxy, amide, nitro, trifluoromethyl, halogen or cyano is preferred.

It is preferred that $R_7$ is hydrogen, methyl, alkoxy, nitro, halogen, cyano or an amide group.

Compounds wherein A is 2-substituted pyridyl are of special interest, especially those carrying an methoxy, amide, cyano or hydrogen substituent in the 3-position.

The compounds of formula (I) have basic properties and, consequently, they may be converted to their therapeutically active acid addition salts by treatment with appropriated acids; e.g. inorganic acids such as hydrochloric, hydrobromic, sulfuric, nitric and phosphoric acid, or organic acids such as acetic, propanoic, glycolic, lactic, malonic, oxalic, succinic, fumaric, tartaric, citric and pamoic acid.

Conversely, the salt form can be converted into the free base form by treatment with alkali.

The compounds of formula (I) and their pharmaceutically acceptable salts have valuable pharmacological properties, making them useful for the treatment of mental disorders such as psychoses, depression and anxiety. Stress and anxiety in animals can also be treated.

It has been assumed that the antipsychotic actions of neuroleptic drugs are inextricably linked to their ability to produce extrapyramidal side-effects, possibly by an action at a common site. This assumption is now being questioned since antipsychotic drugs nowadays exist with a reduced potential to produce these side-effects. Thus, it is thought that the two main actions of classical neuroleptic drugs, i.e. antipsychotic action and ability to produce extrapyramidal syndromes, are mediated by actions at different sites in the brain. The neuroleptic drugs may produce their therapeutic antipsychotic effects by an action on the mesolimbic system. On the other hand, since the main function of the nigrostriatal dopaminergic pathway is the control of motor performance, this site in the brain is usually assumed to be the region where the neuroleptic drugs produce their extrapyramidal side-effects. Experimentally, inhibition of amphetamine induced hypermotility in rodents measures the limbic effect whereas it is generally accepted that the ability of neuroleptics to induce catalepsy in rodents correlates well with the risk of extrapyramidal side-effects.

The compounds of the present invention show neuroleptic properties since they affect amphetamine-induced hypermotility, but show weak or no cataleptogenic activity. They show a high affinity for $D_2$ and $5\text{-}HT_2$ receptors in the brain. A high $5HT_2$-receptor binding affinity may indicate antidepressant properties, since many antidepressants (e.g. amitriptyline) are potent $5HT_2$-blockers. A high $5HT_2$-receptor binding affinity also suggests anxiolytic properties. A novel anxiolytic, ritanserine, labels preferentially the $5\text{-}HT_2$ binding site.

Effective quantities of any of the foregoing pharmacologically active compounds of formula (I) may be administered to a human being or an animal for therapeutic purposes according to usual routes of administration and in usual forms, such as orally in solutions, emulsions, suspensions, pills, tablets and capsules, in pharmaceutically acceptable carriers and parenterally in the form of sterile solutions. For the parenteral administration of the active substance the carrier of excipient may be a sterile, parenterally acceptable liquid, e.g. water, or a parenterally acceptable oil, e.g. arachidic oil.

Although very small quantities of the active materials of the present invention are effective when minor therapy is involved or in the cases of administration to subjects having a relatively low body weight, unit dosages are usually from 2 milligrams upwards, preferably 10, 25 or 50 milligrams or even higher depending on the condition to be treated and the age and weight of the patients as well as the response to the medication.

The unit dose may be from 0.1 to 100 milligrams, preferably from 10 to 50 milligrams. Daily dosages should preferably range from 10 milligrams to 200 milligrams. The exact individual dosages as well as daily dosages will, of course, be determined according to standard medical principles under the direction of a physician or veterinarian.

METHODS OF PREPARATION

The compounds having the general formula (I) may be prepared by conventional methods.

METHOD 1

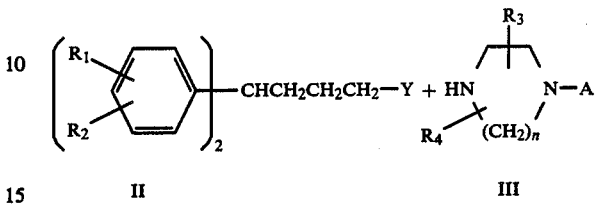

A compound of formula (II), wherein $R_1$ and $R_2$ are as previously defined and Y is a suitable leaving group such as halogen and alkyl- or arylsulfonate is reacted with a compound of formula (III) wherein $R_3$, $R_4$, A and n are as defined previously. The reactions may be carried out using standard N-alkylating procedures.

METHOD 2

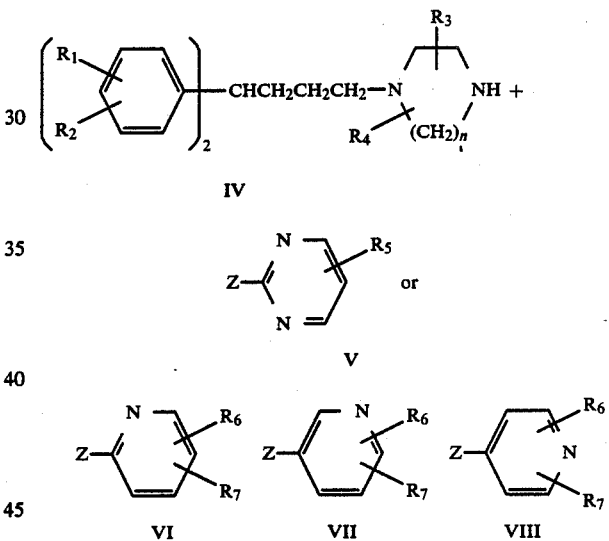

A compound of formula (IV), wherein $R_1$, $R_2$, $R_3$, $R_4$ and n are as perviously defined is reacted with a compound of formula (V), (VI), (VII) or (VIII), wherein $R_5$, $R_6$ and $R_7$ are as previously defined and Z is a leaving group, e.g. halogen.

EXAMPLES

The following examples are intended to illustrate but not to limit the scope of the invention, although the compounds named are of particular interest for our intended purposes. These compounds have been designated by a number code, a:b, where a means the number of the example, wherein the preparation of the compound in question is described, and b refers to the order of the compounds prepared according that example. Thus, compound 1:2 means the second compound prepared according to Example 1.

The structure of the compound are confirmed by NMR, mass-spectra and elementary analysis. When melting points are given, these are uncorrected.

EXAMPLE 1

4-[4,4-bis(p-fluorophenyl)butyl]-1-(5-chloro-2-pyridyl)-piperazine dihydrochloride 19.8 g (0.06 mole) of 1-[4,4-bis(p-fluorophenyl)butyl]-piperazine and 2.96 g (0.02 mole) of 2,5-dichloropyridine were heated together with 2 ml of toluene at 130° C. (temperature of oil bath) for 20 h.

After cooling the reaction mixture was partitioned between ligroin and MeOH/H$_2$O (3:1). The MeOH/H$_2$O phase was extracted an additional time with ligroin and the collected ligroin phases were dried with Na$_2$SO$_4$. Evaporation of the solvents yielded crude free base, which was dissolved in ether and the hydrochloride was precipitated with excess HCl in EtOH. Recrystallization from EtOAc/EtOH yielded 4.3 g (42%) of the title compound (1:1), m.p. 173°–6°.

Using essentially the same procedure the following compounds were prepared (isolated as the free bases or as the corresponding salts) from the corresponding starting materials.

| | |
|---|---|
| 1:2 | 4-[4,4-bis(p-fluorophenyl)butyl]-1-(6-methyl-2-pyridyl)-piperazine oxalate, m.p. 172–4° C. |
| 1:3 | 4-[4,4-bis(p-fluorophenyl)butyl]-1-(6-methoxy-2-pyridyl)-piperazine fumarate, m.p. 175–7° C. |
| 1:4 | 4-[4,4-bis(p-fluorophenyl)butyl]1-(3-trifluoromethyl-2-pyridyl)-piperazine, monohydrochloride isopropanol, m.p. 94–95° C. (sintered) |
| 1:5 | 4-[4,4-bis(p-fluorophenyl)butyl]-1-(5-trifluoromethyl-2-pyridyl)-piperazine monohydrochloride m.p. 197–9° C. |
| 1:6 | 4-[4,4-bis(p-fluorophenyl)butyl]-1-(3-carbamoyl-2-pyridyl)piperazine dihydrochloride, m.p. 208–10° C. |
| 1:7 | 4-[4,4-bis(p-fluorophenyl)butyl]-1-(5-carbamoyl-2-pyridyl)-piperazine dihydrochloride, m.p. 250° C. |
| 1:8 | 4-[4,4-bis(p-fluorophenyl)butyl]-1-[3-(N-methylcarbamoyl)-2-pyridyl]-piperazine dihydrochloride d. 185° C. |
| 1:9 | 4-[4,4-bis(p-fluorophenyl)butyl]-1-[3-(N,N-dimethyl-carbamoyl)-2-pyridyl]-piperazine fumarate m.p. 182–3° C. |
| 1:10 | 4[4,4-bis(p-fluorophenyl)butyl]-1-(3-morpholinocarbonyl-2-pyridyl)-piperazine oxalate m.p. 183–5° C. |
| 1:11 | 4-[4,4-bis(p-fluorophenyl)butyl]-1-(3-pyrrolidinocarbonyl-2-pyridyl)-piperazine fumarate m.p. 194–5° C. |
| 1:12 | 4-[4,4-bis(p-fluorophenyl)butyl]-1-(3-cyano-2-pyridyl)piperazine oxalate m.p. 180–1° C. |
| 1:13 | 4-[4,4-bis(p-fluorophenyl)butyl]-1-(3-nitro-2-pyridyl)-piperazine monohydrochloride, mp. 147–8° C. |
| 1:14 | 4-[4,4-bis(p-fluorophenyl)butyl]-1-(5-nitro-2-pyridyl)-piperazine hydrochloride m.p. 214–6° C. |
| 1:15 | 4-[4,4-bis(p-fluorophenyl)butyl]-1-(2-pyridyl)-(1,4-diaza-cycloheptane) × 2.5 oxalate m.p. 115–8° C. |
| 1:16 | 4-[4,4-bis(p-fluorophenyl)butyl]-(2-pyridyl)-trans-2,5-dimethylpiperazine oxalate m p. 141–2° C. |
| 1:17 | 4-[4,4-bis(p-fluorophenyl)butyl]-1-[2-(methylpyridine-5-carboxylate)-yl]piperazine dihydrochloride ethanol m.p. 153 (sintered) |
| 1:18 | 4-[4,4-bis(p-fluorophenyl)butyl]-1-(4-pyridyl)-piperazine difumarate m.p. 191–2° C. |
| 1:19 | 4-[4,4-bis(p-fluorophenyl)butyl]-1-(3-methyl-2-pyridyl piperazine dihydrochloride hemi-isopropanol m.p. 207–9° C. |
| 1:20 | 4-[4,4-bis(p-fluorophenyl)butyl]-1-(3-methoxy-2-pyridyl)-piperazine oxalate d. 187–8° C. |
| 1:21 | 4-[4,4-bis(p-fluorophenyl)butyl]-1-(6-chloro-2-pyridyl)-piperazine hydrochloride m.p. 172–3° C. |
| 1:22 | 4-[4,4-bis(p-fluorophenyl)butyl]-1-(3-chloro-2-pyridyl)-piperazine fumarate m.p. 145–6° C. |
| 1:23 | 4-[4,4-bis(p-fluorophenyl)butyl]-1-(3-carboxy-2-pyridyl)-piperazine dihydrochloride ethanol m.p. 185° C. (sinters) m.p. 210° C. |
| 1:24 | 4-[4,4-bis(p-fluorophenyl)butyl]-1-[3-(4-methylpiperidinocarbonyl)-2-pyridyl]-piperazine fumarate m.p. 191–2° C. |
| 1:25 | 4-[4,4-bis(p-fluorophenyl)butyl]-1-(3-carbamyl-2-pyridyl)-1,4-diazacycloheptane dihydrochloride hemihydrate m.p. 176–79° C. (sintered) 1:26 4-[4,4-bis(p-fluorophenyl)butyl]-1-(3-trifluoromethyl-6-chloro-2-pyridyl)-piperazine hydrochloride m.p. 141–2° C. |
| 1:27 | 4-[4,4-bis(3,4-difluorophenyl)butyl(-1-(2-pyridyl)-piperazine dihydrochloride, hydrate m.p. 169–70° C. |
| 1:28 | 4-[4,4-bis(p-fluorophenyl)butyl[-1-(3-hydroxy-2-pyridyl)-piperazine |
| 1:29 | 4-[4,4-bis(p-fluorophenyl)butyl]-1-(3-pyridyl)-piperazine |
| 1:30 | 4-[4,4-bis(p-fluorophenyl)butyl]-1-(3-carbamoyl-6-methyl-2-pyridyl)piperazine |
| 1:31 | 4-[4,4-bis(p-fluorophenyl)butyl]-1-(3-carbamoyl-6-chloro-2-pyridyl)piperazine |
| 1:32 | 4-[4,4-bis(p-fluorophenyl)butyl]-1-(4-methyl-2-pyridyl)piperazine |
| 1:33 | 4-[4,4-bis(p-fluorophenyl)butyl]-1-(3-ethoxy-2-pyridyl)-piperazine |
| 1:34 | 4-[4,4-bis(p-fluorophenyl)butyl] -1-(3-propoxy-2-pyridyl)-piperazine |
| 1:35 | 4-[4,4-bis(p-fluorophenyl)butyl]-1-(3-isopropoxy-2-pyridyl)-piperazine |
| 1:36 | 4-[4,4-bis(p-fluorophenyl)butyl]-1-(3-cyclohexoxy-2-pyridyl)-piperazine |

EXAMPLE 2

4-[4,4-bis(p-fluorophenyl)butyl]-1-(2-pyrimidyl)-piperazine hydrochloride 8.3 g (0.025 mole) of 1-[4,4-bis(p-fluorophenyl)butyl]-piperazine and 3.1 g (0.027 mole) of 2-chloropyrimidin were heated in 5 ml DMF at 150° C. until TLC showed the disappearance of the starting piperazine derivative. After cooling EtOAc (50 ml) and EtOH (enough to get a clear solution) were added. Ether was added, whereby the desired product crystallized. Recrystallization from EtOH, EtOAc+ether yielded 7.3 g (65%) of the title compound (2:1), m.p. 195°–97° C.

EXAMPLE 3

4-[4,4-bis(p-fluorophenyl)butyl]-1-(2-pyridyl)-piperazine dihydrochloride 3.3 g (0.01 mole) of 1-chloro-4,4-bis(p-fluorophenyl)-butane, 3.3 g (0.02 mole) of 1-(2-pyridyl)-piperazine and 0.05 g of KI were refluxed in 15 ml of toluene for 48 h. After cooling and addition of ether (30 ml) 1-(2-pyridyl)-piperazine hydrochloride precipitated and was filtered off. After subsequent washing several times with H$_2$O the organic layer was dried with K$_2$CO$_3$. Evaporation of the solvent yielded the crude base. This was dissolved in ether and HCl in EtOH was added to precipitate the hydrochloride. Recrystallization from EtOAc/EtOH yielded 3.2 g (67%) of the title compound (2:1), m.p. 224°–27° C.

Using essentially the same procedure the following compounds are prepared (isolated as the free bases or as the corresponding salts) from the corresponding starting materials.

| | |
|---|---|
| 3:2 | 4-[4,4-bis(p-fluorophenyl)butyl]-1-(5-fluoro-2-pyrimidyl)-piperazine |

EXAMPLE 4

This example illustrates the potency of compounds of formula (I) and their pharmaceutically active salts for treatment of metal disorders.

TEST 1

Antagonism of amphetamine-induced hypermotility in mice

A low dose (2 mg/kg) of d-amphetamine administered to mice induced pronounced locomotor activity.

Test procedure

Female NMRI-mice, weighing about 25 g are divided into groups of 4 animals and placed in macrolon cages. The cages are placed on recording arenas in nine sound attenuated boxes with constant light and ventilation. After a familiarization period of 90 minutes the mice are brought up from the cages and treated in the following way; one control group receives saline i.p., one control group receives d-amphetamine sulphate, 2 mg/kg i.p. and test animals are treated s.c. with three different doses of the test compound and immediately thereafter with d-amphetamine 2 mg/kg i.p. Immediately after the administration the macrolon cages with the mice are put back into the test boxes and a computerized equipment records the locomotor activity in the cages for 90 minutes.

For each test compound 4 cages are treated with saline, 4 cages with only d-amphetamine and 6 cages/dose test compound+d-amphetamine. This is the total of three different experiments.

Data analysis

For each treatment group the mean number of counts during 90 minutes following the administration is calculated.

The $ED_{50}$-value (mg/kg) is calculated from the dose-response curve by means of linear regression. The $ED_{50}$-value represents a dose of test compound reducing the motility to the midpoint between amphetamine and saline controls.

TEST 2

Affinity to $D_2$-receptors

The binding assay is carried out essentially as described by Leysen et al., (Mol. Pharmacol. 21, 301–14, 1982) using $^3H$-spiroperidol as ligand.

TEST 3

Affinity to $5HT_2$-receptors

The binding assay is carried out essentially as described by Leysen et al., (Mol. Pharmacol. 21, 301–14, 1982) using $^3H$-ketanserine as ligand.

TABLE 1

Antagonism of amphetamine induced hypermotility in mice

| Compound | $ED_{50}$ mg/kg s.c. |
|---|---|
| 3:1 | 0.1 |
| 1:6 | 0.3 |

TABLE 2

Affinity to $D_2$-receptors

| Compound | Ki (nM) |
|---|---|
| 3:1 | 60 |
| 1:6 | 30 |
| 1:15 | 25 |

TABLE 3

Affinity to $5HT_2$-receptors

| Compound | Ki (nM) |
|---|---|
| 3:1 | 5.8 |
| 1:6 | 2.1 |
| 1:15 | 1.3 |

The compounds listed in table 1, 2 and 3 are not given for the purpose of limiting the invention thereto but only to exemplify the useful pharmacological activities of compounds within the scope of formula (I).

EXAMPLE 5

The following formulations are representative for all of the pharmacologically active compounds of this invention. Example of a suitable capsule formulation:

|  | Per capsule, mg |
|---|---|
| Active ingredient, as salt | 10 |
| Lactose | 250 |
| Starch | 120 |
| Magnesium stearate | 5 |
| Total | 385 |

In case of higher amounts of active ingredient, the amount of lactose used may be reduced.

Example of a suitable tablet formulation:

|  | Per tablet, mg |
|---|---|
| Active ingredient, as salt | 10 |
| Potato starch | 90 |
| Colloidal Silica | 10 |
| Talc | 20 |
| Magnesium stearate | 2 |
| 5% aqueous solution of gelatin | 25 |
| Total | 157 |

Solutions for parenteral applications by injection can be prepared in an aqueous solution of a water-soluble pharmaceutically acceptable salt of the active substance preferably in a concentration of from about 0.5% to about 5% by weight. These solutions may also contain stabilizing agents and/or buffering agents and may conveniently be provided in various dosage unit ampoules.

We claim:

1. A compound having the formula (I)

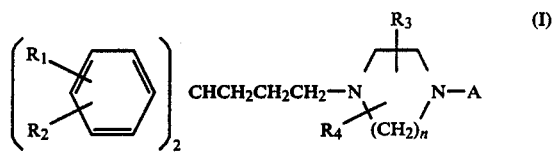

wherein
$R_1$ and $R_2$ are the same or different and selected from hydrogen and halogen;
$R_3$ and $R_4$ are the same or different and selected from hydrogen and lower alkyl;
n is 2 or 3;
A is selected from the following pyrimidyl or pyridyl groups:

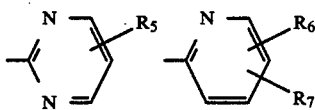 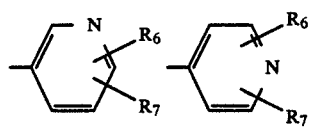

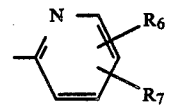

wherein
R₅ is selected from hydrogen, lower alkyl or halogen;
R₆ and R₇ are the same or different and selected from hydrogen, halogen, lower alkyl, lower alkoxy or hydroxy groups, cyano, nitro, trifluoromethyl, COOR₈, CONR₉R₁₀ or CO-B; wherein R₈ is hydrogen or lower alkyl; R₉ and R₁₀ are the same or different and selected from hydrogen, lower alkyl and C₃₋₈;
B is selected from

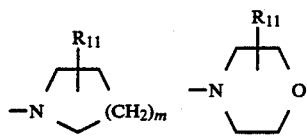

wherein m is 1, 2, 3, or 4,
R₁₁ is selected from hydrogen or lower alkyl, or a pharmacologically active salt thereof.

2. Compounds according to claim 1 wherein one of R₁ and R₂ is halogen, preferably fluoro.

3. Compounds according to claim 1 or 2, wherein R₃ and R₄ are hydrogen or methyl, preferably hydrogen.

4. Compounds according to claim 1 or 2, wherein A is

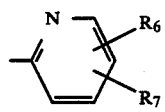

5. Compounds according to claim 4, wherein R₆ is hydrogen, methyl, trifluoromethyl, alkoxy, amide, nitro or cyano and R₇ is hydrogen, methyl, methoxy, nitro, halogen, cyano or an amide group.

6. Compounds according to claim 5, wherein R₆ is hydrogen, methyl, or trifluoromethyl and R₇ is alkoxy, nitro, halogen, cyano or an amide group and R₇ is situated in the 3-position.

7. Compounds according to claim 6, wherein R₆ is hydrogen and R₇ is hydrogen, cyano, nitro, alkoxy or an amide substituent.

8. Compounds according to claim 7 wherein R₇ is an amide, hydrogen, cyano or methoxy substituent.

9. The compounds according to claim 3 wherein A is

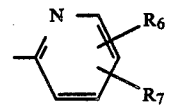

10. The compounds according to claim 9, wherein R₆ is hydrogen, methyl, trifluoromethyl, alkoxy, amide, nitro or cyano and R₇ is hydrogen, methyl, methoxy, nitro, halogen, cyano or an amide group.

11. The compounds according to claim 10, wherein R₆ is hydrogen, methyl, or trifluoromethyl and R₇ is alkoxy, nitro, halogen, cyano or an amide group and R₇ is situated in the 3-position.

12. The compounds according to claim 11 wherein R₆ is hydrogen and R₇ is hydrogen, cyano, nitro, alkoxy or an amide substituent.

13. The compounds according to claim 12, wherein R₇ is an amide, hydrogen, cyano or methoxy substituent.

14. A pharmaceutical composition containing as an active ingredient one or more of the compounds having the formula (I), preferably together with a pharmaceutically acceptable carrier, wherein the effective amount of said active ingredient is from 0.1 mg to 100 mg per unit dose.

15. A pharmaceutical composition containing as an active ingredient one or more of the compounds having the formula (I), preferably together with a pharmaceutically acceptable carrier and, if necessary, other pharmacologically active agents, wherein the effective amount of said ingredient is from 0.1 mg to 100 mg per unit dose.

16. A method of treating a living body suffering from psychoses, depression, stress or anxiety, which comprises the step of administering to said living body a compound having the formula (I).

* * * * *

UNITED STATES PATENT AND TRADEMARK OFFICE
CERTIFICATE OF CORRECTION

PATENT NO. : 4,937,245

DATED : June 26, 1990

INVENTOR(S) : Tomas Fex, et al.

It is certified that error appears in the above-identified patent and that said Letters Patent is hereby corrected as shown below:

Column 6, line 16: "pyridyl)piperazine" should read as --pyridyl)-piperazine--

Signed and Sealed this

Third Day of December, 1991

*Attest:*

HARRY F. MANBECK, JR.

*Attesting Officer*   *Commissioner of Patents and Trademarks*

UNITED STATES PATENT AND TRADEMARK OFFICE
CERTIFICATE OF CORRECTION

PATENT NO. : 4,937,245

DATED : June 26, 1990

INVENTOR(S) : Tomas Fex, et al.

It is certified that error appears in the above-identified patent and that said Letters Patent is hereby corrected as shown below:

Column 9, line 21: "$C_{3-8}$:" should read as --$C_{3-8}$ cycloalkyl;--

Signed and Sealed this

Eighth Day of September, 1992

*Attest:*

DOUGLAS B. COMER

*Attesting Officer*    Acting Commissioner of Patents and Trademarks